(12) United States Patent
Yamada

(10) Patent No.: US 7,708,869 B2
(45) Date of Patent: May 4, 2010

(54) GAS SENSOR

(75) Inventor: Kouhei Yamada, Oobu (JP)

(73) Assignee: Denso Corporation, Kariya (JP)

( * ) Notice: Subject to any disclaimer, the term of this patent is extended or adjusted under 35 U.S.C. 154(b) by 321 days.

(21) Appl. No.: 11/898,761

(22) Filed: Sep. 14, 2007

(65) Prior Publication Data
US 2008/0073209 A1 Mar. 27, 2008

(30) Foreign Application Priority Data
Sep. 21, 2006 (JP) .............................. 2006-255447

(51) Int. Cl.
*G01N 27/407* (2006.01)
(52) U.S. Cl. ..................... 204/428; 73/23.32
(58) Field of Classification Search ................ 204/424, 204/428; 73/23.31, 23.32, 31.05
See application file for complete search history.

(56) References Cited

U.S. PATENT DOCUMENTS

| | | | |
|---|---|---|---|
| 6,346,179 B1 | 2/2002 | Makino et al. | |
| 2002/0100312 A1* | 8/2002 | Jackson et al. | ............. 73/31.05 |
| 2003/0136675 A1* | 7/2003 | Ishikawa | ..................... 204/424 |
| 2004/0144645 A1* | 7/2004 | Yamada et al. | .............. 204/424 |
| 2005/0178187 A1* | 8/2005 | Nakagawa | ................. 73/31.05 |
| 2007/0251823 A1* | 11/2007 | Yamada | ...................... 204/424 |
| 2008/0016948 A1* | 1/2008 | Yamada | ..................... 73/31.05 |

FOREIGN PATENT DOCUMENTS

| | | |
|---|---|---|
| JP | 2001-099807 | 4/2001 |
| JP | 2004-245103 | 9/2004 |

\* cited by examiner

*Primary Examiner*—Kaj K Olsen
(74) *Attorney, Agent, or Firm*—Nixon & Vanderhye PC

(57) ABSTRACT

A gas sensor has a sensor element detecting a concentration of a specified gas, a housing fixing this element to a gas pipe to expose it to measuring-gas flow, and cylindrical inner and outer covers of a different radius, configured in concentric configuration, having a base part. Side surface openings are formed in the inner cover so that each opening turns upward from the outside to the inside of the inner cover. Openings are formed in the bottom surface of the inner cover around a circle in concentric with the inner cover. Openings are formed in the side surface of the outer cover through which the measuring gases are introduced into a gap between the inner and outer covers. A gap is formed between bottom surfaces of both the covers. An opening is formed at the center of the bottom surface of the outer cover.

18 Claims, 11 Drawing Sheets

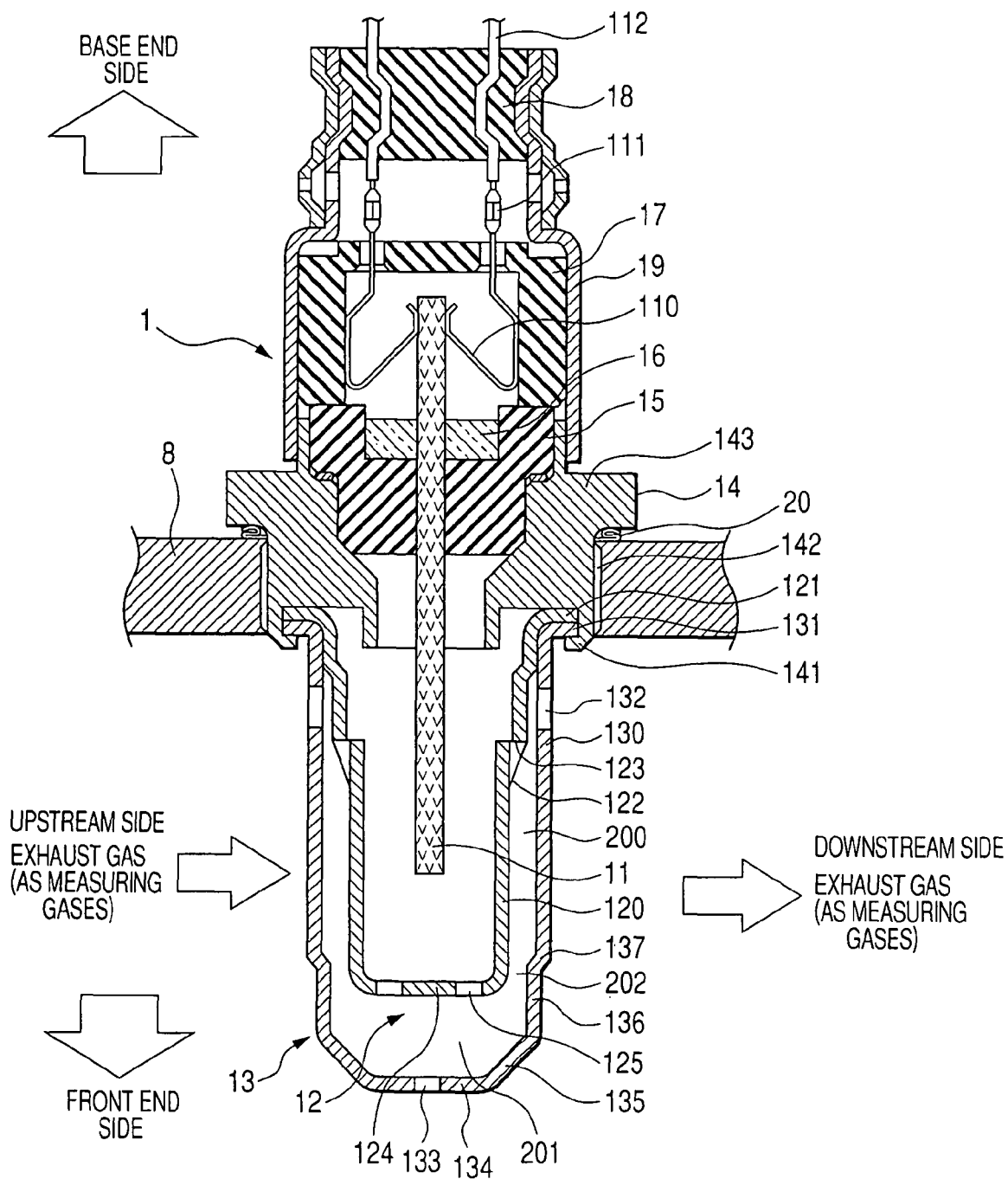

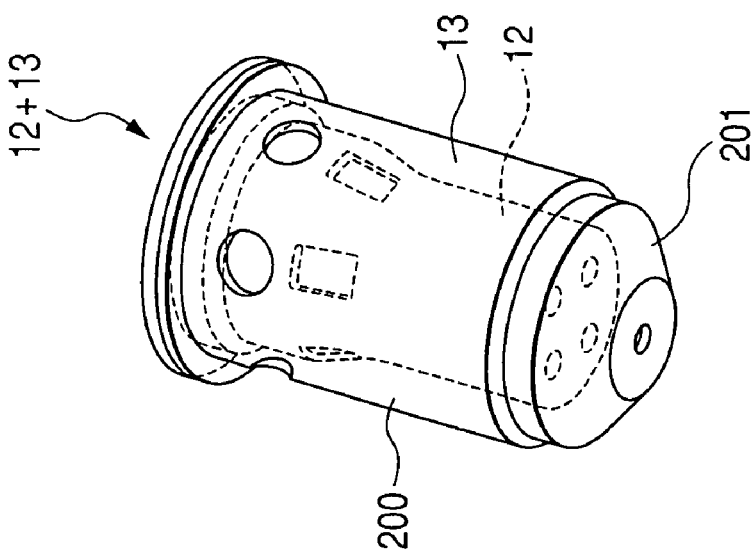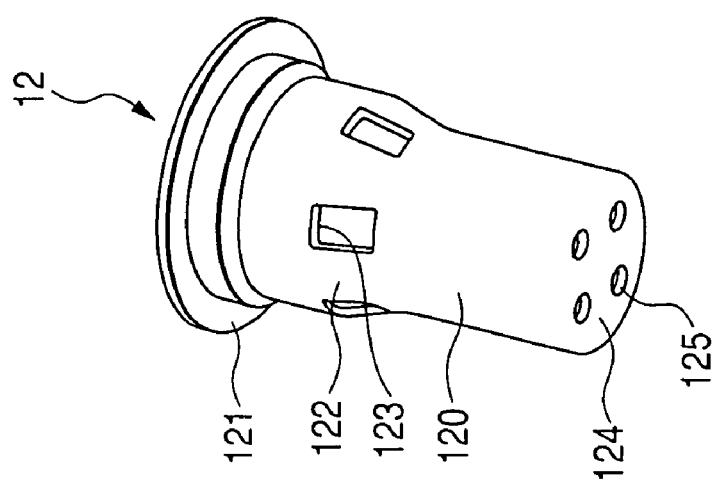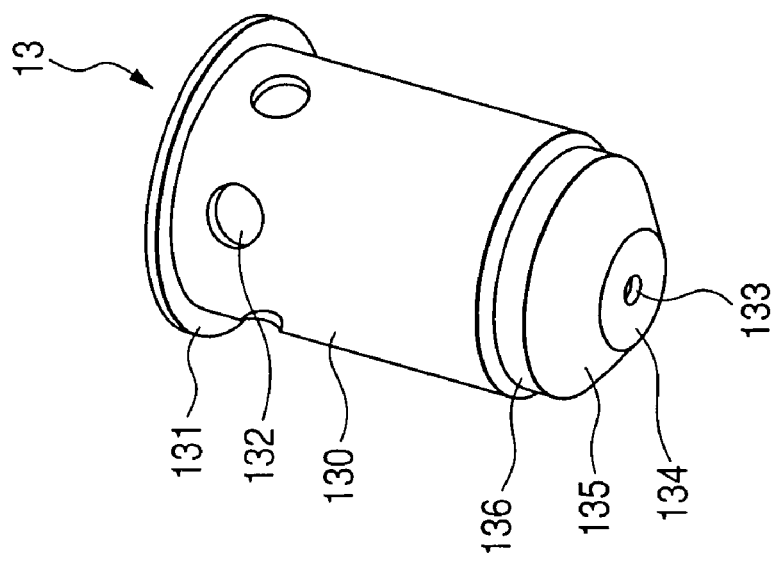

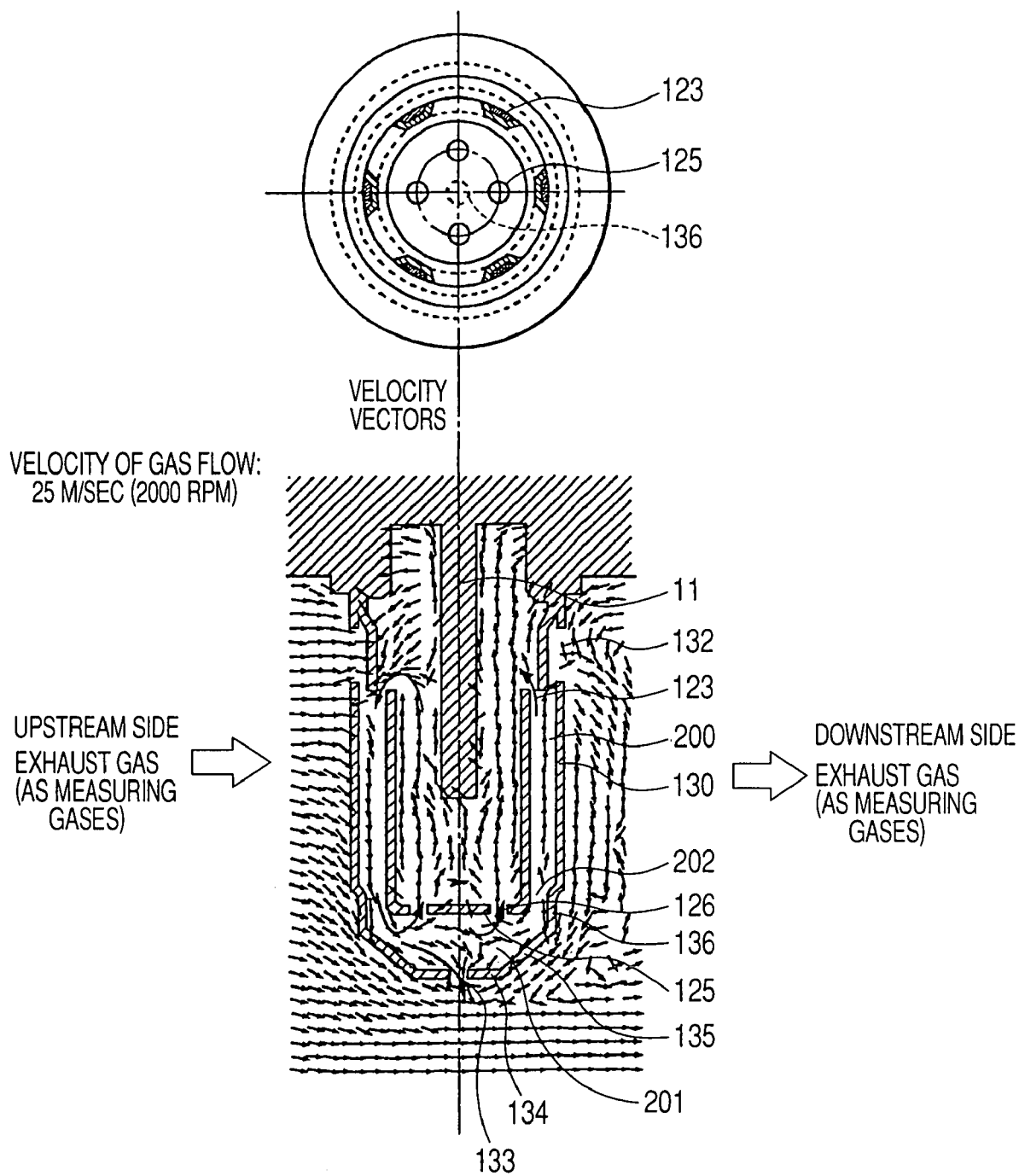

FIG. 4A
WATER PROOF CAPABILITY EVALUATION APPARATUS
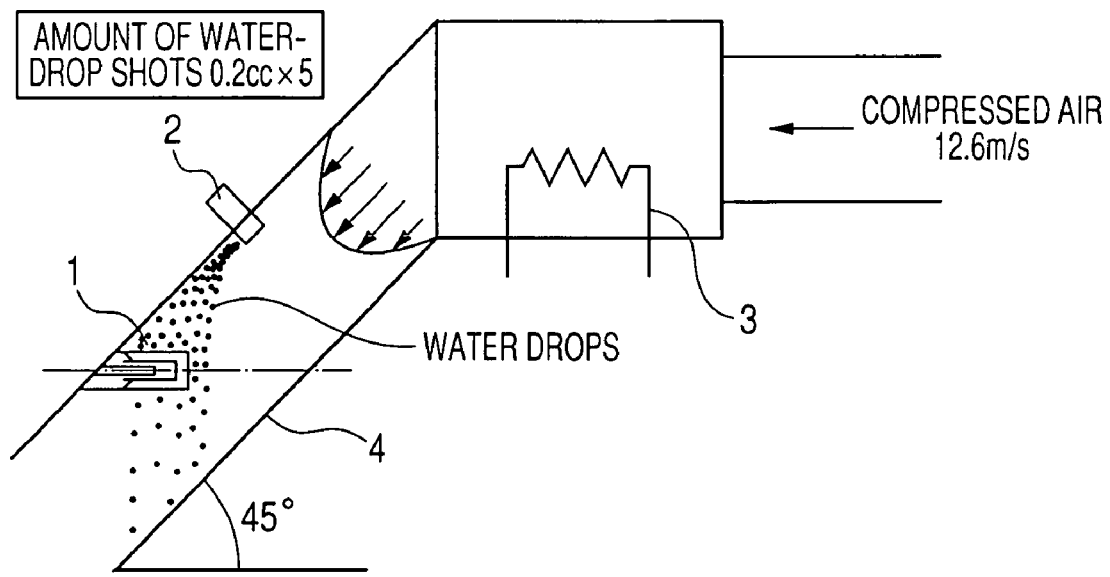
FIG. 4B
MANNER OF VERIFYING WATER PROOF CAPABILITY
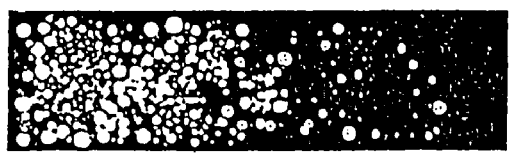

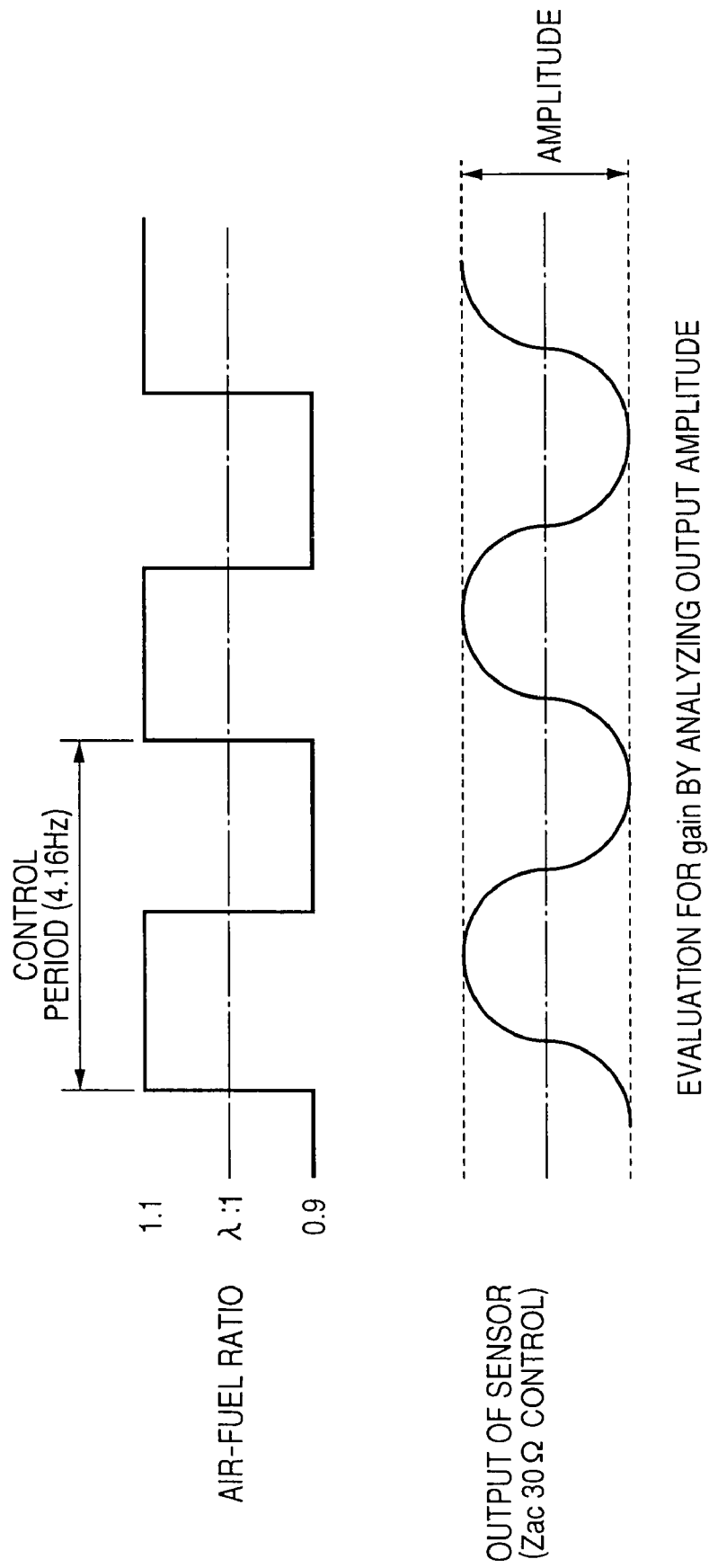

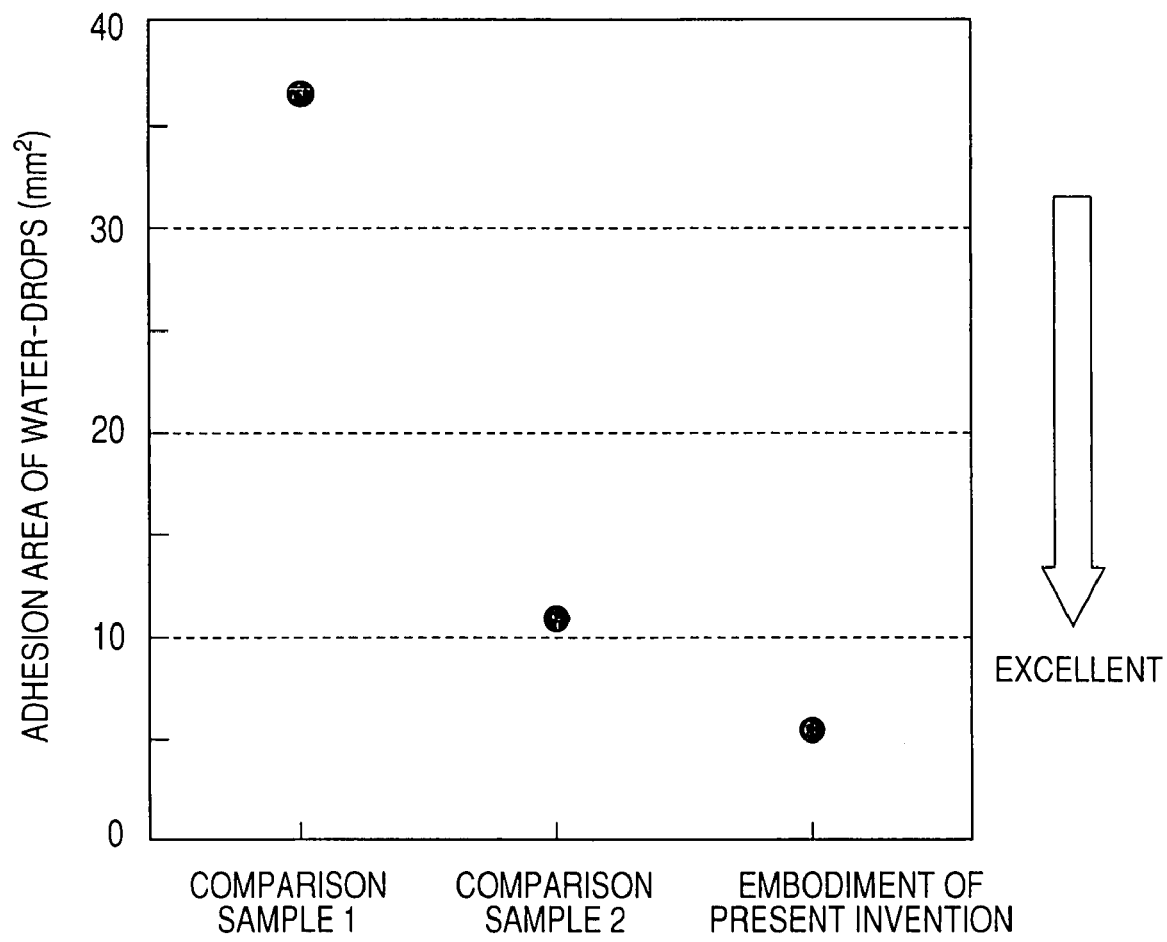

THREE BOTTOM SURFACE OPENING PARTS OF INNER COVER

FOUR BOTTOM SURFACE OPENING PARTS OF INNER COVER

FIVE BOTTOM SURFACE OPENING PARTS OF INNER COVER

SIX BOTTOM SURFACE OPENING PARTS OF INNER COVER

GAS SENSOR

CROSS-REFERENCE TO RELATED APPLICATION

This application is related to and claims priority from Japanese Patent Application No. 2006-255447 filed on Sep. 21, 2006, the contents of which are hereby incorporated by reference.

BACKGROUND OF THE INVENTION

1. Field of the invention

The present invention relates to a gas sensor capable of detecting a concentration of a specific gas contained in measuring gases such as exhaust gas discharged from internal combustion engines such as engines of motor vehicles, in particular, relates to a structure of a protection cover capable of protecting a gas sensor element in a gas sensor.

2. Description of the Related Art

A recent vehicle is equipped with a gas sensor including a gas sensor element capable of detecting a concentration of a specific gas contained in measuring gases, for example, oxygen contained in exhaust gas emitted from an internal combustion engine of a vehicle. An electric control unit (ECU) mounted on such a vehicle receives a detection signal regarding the concentration of oxygen and other gas transferred from the gas sensor, and calculates an air-fuel ratio of the vehicle based on the concentration of oxygen detected. The ECU then controls the combustion or burning operation of the internal combustion engine based on the calculated air-fuel ratio. In general, the gas sensor has the gas sensor element which is inserted and placed in a housing thereof. The gas sensor is fixed to the wall of an exhaust gas flowing passage. A front end part of the gas sensor element in the gas sensor projects to or is exposed to gas flow in the exhaust gas flowing passage. In the gas sensor, the gas sensor element is covered with a protection cover fixed to the housing so as to protect it from the exhaust gas which is flowing through the exhaust gas flowing passage.

On starting the internal combustion engine under a low temperature environment, the thermal energy of moisture contained in the exhaust gas is absorbed by the cooled exhaust gas flowing passage or pipe and the moisture in the exhaust gas is thereby condensed. The condensed moisture becomes drops of water (hereinafter, referred to as "water-drops"). The water-drops move in the exhaust gas flowing passage or pipe without vaporization to the gas sensor. The exhaust gas containing water-drops then enters into the gas sensor. In this case, there is a possibility of contacting the water-drops contained in the exhaust gas as measuring gases onto the surface of the gas sensor element in the gas sensor.

On measuring the concentration of oxygen and other gases contained in the exhaust gas, the gas sensor element composed mainly of a solid polymer electrolyte membrane is heated at a temperature of more than 400° C. by a heater and the like in order to keep its optimum activation state. In the optimum activation state of the gas sensor element, there is a possibility of generating cracks in the gas sensor element by thermal shock when water-drops enter into the gas sensor and then adhered onto the surface of the gas sensor element.

Because there is a need to have a gas sensor of a high responsiveness in order to enhance the accuracy of controlling the combustion of the internal combustion engine, it is necessary to suck or introduce the exhaust gas into the gas sensor as fast as possible, in order to achieve the quick responsiveness of the gas sensor. There is therefore a need that the cover body covering the gas sensor element has different types of characteristics, the water proof capability (anti-adhesion capability of water-drops) and the high responsiveness, which are inconsistent with to each other.

Japanese patent laid open publication JP 2004-245103 has disclosed a gas sensor composed mainly of a cover body and a gas sensor element. The cover body has a double cylindrical construction composed of an inner cover and an outer cover which has a different radius placed in concentric configuration. In such a gas sensor, each of the inner cover and the outer cover has gas introduction holes, in order to increase its responsiveness, through which measuring gases are introduced into the gas sensor. A gap or a clearance between the inner cover and the outer cover in the gas sensor is set within a specified constant range in order to prevent entering water-drop components contained in the measuring gases through the side surface of the cover body.

The inventor according to the present invention has proposed two types of gas sensors, which have been disclosed in JP 2006-124074 and JP 2006-199073, having a cover body of an improved water proof capability.

FIG. 10 shows a configuration of the gas sensor 1b disclosed in the former proposal JP 2006-124074, and FIG. 11 shows a configuration of the gas sensor 1c disclosed in the latter proposal JP 2006-199073.

As shown in FIG. 10, the cover body of the gas sensor 1b accommodating and covering the gas sensor element 11 has a double cylindrical configuration composed mainly of an inner cover 12b and an outer cover 13b having a different radius. The inner cover 12b and the outer cover 13b are constructed in concentric configuration. In the gas sensor 1b, opening parts 123 are formed at the upper side surface of the inner cover 12b so that the opening direction of each opening part 123 turns upward from the outside to the inside of the inner cover 12b. An opening part 126b is formed at the middle part of a bottom surface 125b of the inner cover 12b. Further, a plurality of side opening parts 132 are formed at the upper side of the side surface of the outer cover 13b. Through the opening parts 132, the measuring gases such as exhaust gas are introduced into the gas sensor element 11. An opening part 133b is formed at the middle part of the bottom surface 135b of the outer cover 13b so that the opening part 133b is in concentric with the opening part 126b of the inner cover 12b.

In the gas sensor 1b shown in FIG. 10, because each opening parts 123 in the side surface of the inner cover 12b is so formed that it turns upward, this configuration of the opening parts 123 prevents invading water-drops into the inner cover 12b, which is introduced with the exhaust gas through the opening part 132 formed in the side surface of the outer cover 13b. The water-drops contained in the exhaust gas fall to the bottom surface 125b through the inner wall of a radius-decreased part 124b formed at the front part of the inner cover 12b. The exhaust gas is finally discharged through the opening part 126b in the bottom surface 125b of the inner cover 12b to the outside of the gas sensor 1b.

The opening part 126b in the bottom surface 125b of the inner cover 12b is formed in a same surface (see FIG. 10) of the opening part 133b in the bottom surface of the outer cover 13b, and protrudes toward the downward when compared with the opening part 133b in the bottom surface of the outer cover 13b in order to achieve a high responsiveness.

On the contrary, the cover body covering the gas sensor element in the gas sensor 1c shown in FIG. 11 has a double cylindrical structure in which the inner cover 12c and the outer cover 13c have a different radius and configured in concentric configuration. In the gas sensor 1c, a side gap 200c is formed between the outer circumference surface of the inner cover 12c and the inner circumference surface of the outer cover 13c, and the opening part 123 at the upper part of the side surface of the inner cover 12c turns upward from the outer part of the inner cover 12c toward the inner part of the inner cover 12c. The opening part 126c is formed at the middle part of the bottom surface 125c of the inner cover 12c. A plurality of opening parts 132 is formed at the upper part of the side surface of the outer cover 13c, through which measuring gases such as exhaust gas are introduced into the side gap 200c.

The bottom surface 134c of the outer cover 13c is placed in position below the bottom surface 125c of the inner cover 12c. A bottom gap 201c is formed between the bottom surface 125c of the inner cover 12c and the bottom surface 134c of the outer cover 13c. A plurality of opening parts 133c is formed at the bottom surface of the outer cover 13c which is positioned outward from the opening part 126c in the bottom surface of the inner cover 12c.

In the gas sensor 1c having the above configuration, the measuring gases such as exhaust gas are introduced or sucked into the side gap 200c through the opening parts 132 formed in the side surface at the upper part of the outer cover 13c, and then flow to the opening part 133c in the bottom surface of the outer cover 13c. Because the opening parts 123 in the inner cover 12c open upward to the inner cover 12c, even if water-drop is contained in the measuring gases such as exhaust gas, the water-drop does not enter the opening parts 123 formed in the side surface of the inner cover 12c and only the measuring gases such as exhaust gas are introduced into the inside of the inner cover 12c. Hence, the water-drop contained in the measuring gases such as exhaust gas introduced through the opening parts 132 in the side surface of the outer cover 13c is quickly discharged to the outside of the gas sensor 1c through the opening part 133c in the bottom surface of the outer cover 13c. It is thereby difficult to adhere or contact the water-drop contained in the measuring gases to the gas sensor element 11 for detecting the gas concentration.

Still further, because the opening part 126c in the bottom surface of the inner cover 12c does not directly contacts to the opening part 133c in the bottom surface of the outer cover 13c, even if a water-drop enters the inside of the outer cover 13c through the opening parts 133c in the bottom surface of the outer cover 13c, the water-drop does not directly enters the inside of the inner cover 12c and the water-drop is evaporated in the bottom gap 201c formed between the bottom surface 125c of the inner cover 12c and the bottom surface 134c of the outer cover 13c. This configuration can avoid the occurrence of entering water-drop to the inside of the gas sensor element 11.

However, in each of the cover bodies composed mainly of the inner over and the outer cover disclosed in JP 2004-245103 and JP 2006-124074 shown in FIG. 10, because the opening part in the bottom surface of the outer cover is constructed in concentric with the opening part in the bottom surface of the inner cover, and the opening part in the bottom surface of the inner cover is exposed to the measuring gases such as exhaust gas, it is difficult to completely prevent the invasion of water-drop into the inner cover through the opening part formed in the bottom surface of the inner cover according to a setting angle or an inclination angle of the gas sensor. In particular, as shown in FIG. 10, when the opening part 126b in the bottom surface of the inner cover 12b and the opening part 133b in the bottom surface of the outer cover 13b are in a same surface, the water-drop stayed in the edges of the opening part 133b in the bottom surface of the outer cover 13b in addition to directly invading water-drops contained in the exhaust gas as measuring gases enter into the inside of the inner cover 12b, and are contacted or adhered to the surface of the gas sensor element 11 when the exhaust gas fast flows.

On the contrary, the gas sensor 1c having the configuration shown in FIG. 11 has a high performance of preventing the invasion of water-drop into the gas sensor element 11. Further, the gas sensor 1c has a highly step response capability which is approximately equal to that of the gas sensor 1b having the configuration shown in FIG. 10 when the flowing speed of the exhaust gas is high. However, the configuration of the inner cover 12c of the gas sensor 1c generates a complicated spiral vortex in the exhaust gas as measuring gases, and generates a negative pressure of a small magnitude, not a large magnitude, which can be generated by the exhaust gas flow in the bottom gap 201c formed at the bottom surfaces 125c and 134c which is necessary for discharging the exhaust gas from the opening part 126c in the bottom surface of the inner cover 12c. Further, when the flow speed of the exhaust gas is low, for example, on starting an internal combustion engine or when a motor vehicle moves at a low speed, the step response capability and a frequency response of the gas sensor 1c become low when compared with those of the gas sensor 1b shown in FIG. 10.

SUMMARY OF THE INVENTION

It is an object of the present invention to provide a gas sensor having a gas sensor element of a superior capability of the water proof (anti-adhesion of water-drop to) for the gas sensor element while maintaining a superior response capability.

To achieve the above purposes, the present invention provides a gas sensor having a concentration detection element, a housing, and a cylindrical cover body. The concentration detection element is capable of detecting a concentration of a specified gas contained in measuring gases which pass through a measuring gas passage. The housing accommodates the concentration detection element and fixes the concentration detection element to the measuring gas passage so that the concentration detection element is exposed in a measuring gas flow. The cylindrical cover body has a bottom part, accommodates a part of the concentration detection element exposed in the measuring gas flow, and the cylindrical cover body has a plural cylinder configuration composed of at least an inner cover and an outer cover of a different radius constructed in a concentric configuration to each other. In the cylindrical cover body, a side surface gap is formed between an outer peripheral surface of the inner cover and an inner peripheral surface of the outer cover. Plural side surface opening parts of the inner cover are formed at the upper part of the side surface of the inner cover so that the opening direction of each side surface opening part of the inner cover turns upward from the outside of the inner cover toward the inside of the inner cover. A plurality of bottom surface opening parts of the inner cover constructed in concentric with an axis of the inner cover is formed in the bottom surface of the inner cover. A plurality of side surface opening parts through which the measuring gases are introduced into the side surface gap is formed at the upper part of the side surface of the outer cover. A bottom surface gap is formed between the bottom surface of the outer cover and the bottom surface of the inner cover in which the bottom surface of the outer cover is positioned below the bottom surface of the inner cover. A bottom surface opening part is formed at a center of the bottom surface of the outer cover, closed in position to the center of the bottom surface rather than the bottom surface opening parts of the inner cover.

The measuring gases to be detected are in general introduced into the side surface gap formed between the outer peripheral surface of the inner cover and the inner peripheral surface of the outer cover through the side surface opening parts of the outer cover which are positioned at the upstream side of the measuring gases. The downward stream of the measuring gases toward the bottom surface opening part of the outer cover is generated in the side surface gap positioned at the upstream side of the measuring gases. On the contrary, the upward stream of the measuring gases toward the side surface opening part of the outer cover are generated in the side surface gap positioned at the downstream side of the measuring gases. The measuring gases are discharged to the outside of the gas sensor through the side surface opening parts of the outer cover positioned at the downstream of the measuring gases.

At this time, the side surface opening part of the inner cover positioned at the upstream side of the measuring gas flow provide a negative pressure by the stream of the measuring gas flow toward the downstream generated in the side surface gap. That is, the side surface opening part of the inner cover acts as an outlet opening of the measuring gases through which the measuring gases introduced in the inner cover are discharged to the side surface gap.

Because the upward stream of the measuring gases is generated in the side surface gap, the side surface opening parts positioned at the downstream side of the measuring gases of the inner cover acts as inlet opening of the measuring gases through which the measuring gases are introduced into the inner cover. The gas stream from the bottom surface gap into the inner cover is generated at the bottom surface opening parts of the inner cover.

Accordingly, the measuring gases introduced from the side surface opening part of the outer cover positioned at the upstream side of the measuring gases are introduced into the inner cover through the bottom part of the inner cover and the side surface opening parts of the inner cover positioned at the downstream side of the measuring gases. The measuring gases are further introduced from the side surface opening parts of the inner cover to the side surface gap, and the measuring gases are then quickly discharged to the outside of the gas sensor from the bottom surface opening part of the outer cover and the side surface opening parts of the outer cover positioned at the downstream side of the measuring gases. Hence, the gas sensor having the above configuration of the present invention has a high response capability.

Because each side surface opening part of the inner cover turns upward from the outside of the inner cover toward the inside of the inner cover, even if water drops are contained in the measuring gases such as exhaust gas discharged from an internal combustion engine, no water drop enters into the side surface opening part of the inner cover, the measuring gases are only introduced into the inner cover and contacted to the gas sensor element. Further, those water drops contained in the measuring gases and entering the gas sensor are forcedly discharged through the bottom surface opening parts of the outer cover, as fast as possible, by a strong downward stream of the measuring gas flow generated in the side surface gap positioned at the upstream side of the measuring gases. This configuration of the gas sensor of the present invention provides a superior water proof capability.

Still further, because the bottom surface opening parts of the inner cover are not joined in a same axis to the bottom surface opening part of the outer cover, even if the water drops enter into the gas sensor through the bottom surface opening part of the outer cover, there is no possibility of directly entering the water drops into the in the inner cover, the water drops are evaporated while moving on the bottom surface gap formed between the bottom surface of the inner cover and the bottom surface of the outer cover. This can avoid the adhesion of those water drops onto the surface of the gas sensor element accommodate by the inner cover.

In the gas sensor as another aspect of the present invention, the outer cover has a tapered part at a front end part of the outer cover, and a radius of the tapered part of the outer cover is gradually decreased toward the front end part of the outer cover.

The measuring gases collide with the tapered part formed at the front ed part of the outer cover and generates the downward stream of the measuring gas flow toward the front end of the outer cover. A pressure difference between the inside of the outer cover and the outside of the outer cover at the bottom surface opening part of the outer cover becomes large. Because this pressure difference increases the magnitude of the negative pressure at the bottom surface opening part of the outer cover, the measuring gases are forcedly discharged through the bottom surface opening part of the outer cover. Accordingly, because the measuring gases introduced into the inner and outer covers are strongly discharged to the outside of the gas sensor, the present invention can provide the gas sensor of a superior response capability.

In the gas sensor as another aspect of the present invention, one of a tapered part and a plurality of concave parts is formed at the upper part of the inner cover where a radius of the tapered part is reduced toward the front end of the inner cover and each concave part is concave toward the inside of the inner cover, and each of the side surface opening parts of the inner cover has a slit shaped opening and is formed in one of the tapered part and the concave part. Because the side surface opening parts of the inner cover have a slit opening, which turns upward toward the base part of the inner cover, formed at the tapered part or the concave part, it is possible to prevent the invasion of water drops into the inner cover, and the present invention can provide the gas sensor of a superior water proof capability.

In the gas sensor as another aspect of the present invention, a radius decreased part is formed at the side surface in a front end part of the outer cover so that the base part of the radius decreased part is larger in radius than the front end part of the radius decreased part, and the side surface gap is small near the bottom surface of the inner cover.

Because the velocity of the gas flow is increased at the narrower part in the side surface gap, the discharging velocity of the measuring gases from the side surface opening parts of the inner cover and the introduction velocity of the measuring gases into the bottom surface opening parts of the inner cover become high, the present invention can provide the gas sensor of a superior response capability.

In the gas sensor as another aspect of the present invention, the bottom surface opening part of the outer cover is a circular shape whose diameter is set within a range of 0.5 mm to 3.0 mm.

Setting the diameter of the bottom surface opening part of the outer cover within the range described above can provide an optimum responsiveness. If the diameter of the bottom surface opening part of the outer cover is smaller than 0.5 mm, it is difficult to discharge the measuring gases from the gas sensor to the outside of the gas sensor through the bottom surface opening part of the outer cover. This deteriorates the responsiveness of the gas sensor capable of detecting the specified gas contained in the measuring gases. On the other hand, if the diameter of the bottom surface opening part of the outer cover exceeds 2.0 mm, water drops contained in the measuring gases are easily introduced into the gas sensor. This configuration of the gas sensor deteriorates the water proof capability.

In the gas sensor as another aspect of the present invention, the bottom surface gap formed between the bottom surface of the inner cover and the bottom surface of the outer cover is set within a range of 0.5 mm to 5.5 mm.

Setting the bottom surface gap within the range described above can provide the optimum responsiveness and a superior water proof capability.

If the bottom surface gap is set to less than 0.5 mm, it is difficult to introduce/discharge the measuring gases into/from the gas sensor through the bottom surface opening part of the outer cover. This configuration of the gas sensor provides a bad responsiveness. On the other hand, if the bottom surface gap exceeds 5.5 mm, the suction force generated at the bottom surface gap becomes weak. This deteriorates the responsiveness of the gas sensor capable of detecting the specified gas contained in the measuring gases.

In the gas sensor as another aspect of the present invention, the plurality of bottom surface opening parts of the inner cover is formed in the bottom surface of the inner cover having a circular shape whose diameter is set within a range of 3.5 mm to 5.5 mm, and the axis of the bottom surface of a circular shape of the inner cover is concentric with the axis of the outer cover.

Setting the position of the bottom surface opening parts of the inner cover within the range described above, it is possible to obtain the optimum responsiveness of the gas sensor and the optimum water proof capability of the gas sensor. If the position of the bottom surface opening parts of the inner cover is inside of the diameter of 3.5 mm, because the configuration of the bottom surface opening parts of the inner cover is approximately equal to the configuration having a single opening part formed at the center of the bottom surface of the inner cover, and further because the bottom surface opening part of the outer cover is concentric with the bottom surface opening part of the inner cover, the gas sensor has no water proof capability. On the other hand, if the position of the bottom surface opening parts of the inner cover is outside of the diameter of 5.5 mm, because this needs to enlarge the outer radius of the outer cover, it is necessary to change the configuration of the various parts forming the gas sensor.

In the gas sensor as another aspect of the present invention, a radius of the opening of each bottom surface opening part of the inner cover has a circular shape whose diameter is set within a range of 0.5 m to 2.0 mm.

Setting the diameter of the bottom surface opening part of the inner cover within the range described above, it is possible to have the optimum responsiveness of and the superior water proof capability of the gas sensor. If the diameter of the bottom surface opening part of the inner cover is less than 0.5 mm, it becomes difficult to introduce/discharge the measuring gases into/from the gas sensor. This configuration of the gas sensor provides a bad responsiveness. On the other hand, if the diameter of the bottom surface opening part of the inner cover exceeds 2.0 mm, water drops entered into the bottom surface gap easily enter into the inner cover, and the water proof capability is thereby decreased. This configuration deteriorates the responsiveness of the gas sensor capable of detecting the specified gas contained in the measuring gases.

In the gas sensor as another aspect of the present invention, the plurality of bottom surface opening parts of the inner cover are at least three openings or more placed at a regular interval in concentric with the axis of the inner cover.

The configuration of the gas sensor described above can provide the optimum responsiveness and the superior water proof capability. If the configuration having only the two bottom part opening parts of the inner cover needs to specify the direction of setting each bottom part opening part. This configuration introduces inconvenience in practical use and is hard to introduce/discharge the measuring gases into/from the gas sensor. Thereby the responsiveness of the gas sensor is decreased.

In the gas sensor as another aspect of the present invention, the side surface gap is set within a range of 0.5 mm to 1.5 mm.

Setting the side surface gap within the range described above can increase the frequency responsiveness of the gas sensor.

According to the present invention, it is possible to provide the gas sensor with the superior responsiveness and the superior water proof capability of the gas sensor element.

BRIEF DESCRIPTION OF THE DRAWINGS

A preferred, non-limiting embodiment of the present invention will be described by way of example with reference to the accompanying drawings, in which:

FIG. 1 is a sectional view showing a configuration of a gas sensor according to an embodiment of the present invention;

FIG. 2A is a perspective view of an outer cover of the gas sensor according to the embodiment;

FIG. 2B is a perspective view of an inner cover of the gas sensor according to the embodiment;

FIG. 2C is a perspective view showing an assembly of the outer cover shown in FIG. 2A and the inner cover shown in FIG. 2B in the gas sensor according to the embodiment;

FIG. 3 is a schematic view showing gas flow vectors of indicating gas flow velocity in the gas sensor according to the embodiment of the present invention;

FIG. 4A shows a water proof testing apparatus as a simulator for performing water proof simulation of the gas sensor;

FIG. 4B shows an evaluation manner of evaluating the experimental results by the simulator shown in FIG. 4;

FIG. 5 is shows an experimental manner of performing a frequency response test in order to verify the effects of the gas sensor;

FIG. 6 shows evaluation results of the gas sensor according to the embodiment of the present invention and comparison examples in water proof capability;

DETAILED DESCRIPTION OF THE PREFERRED EMBODIMENTS

Figure 7:
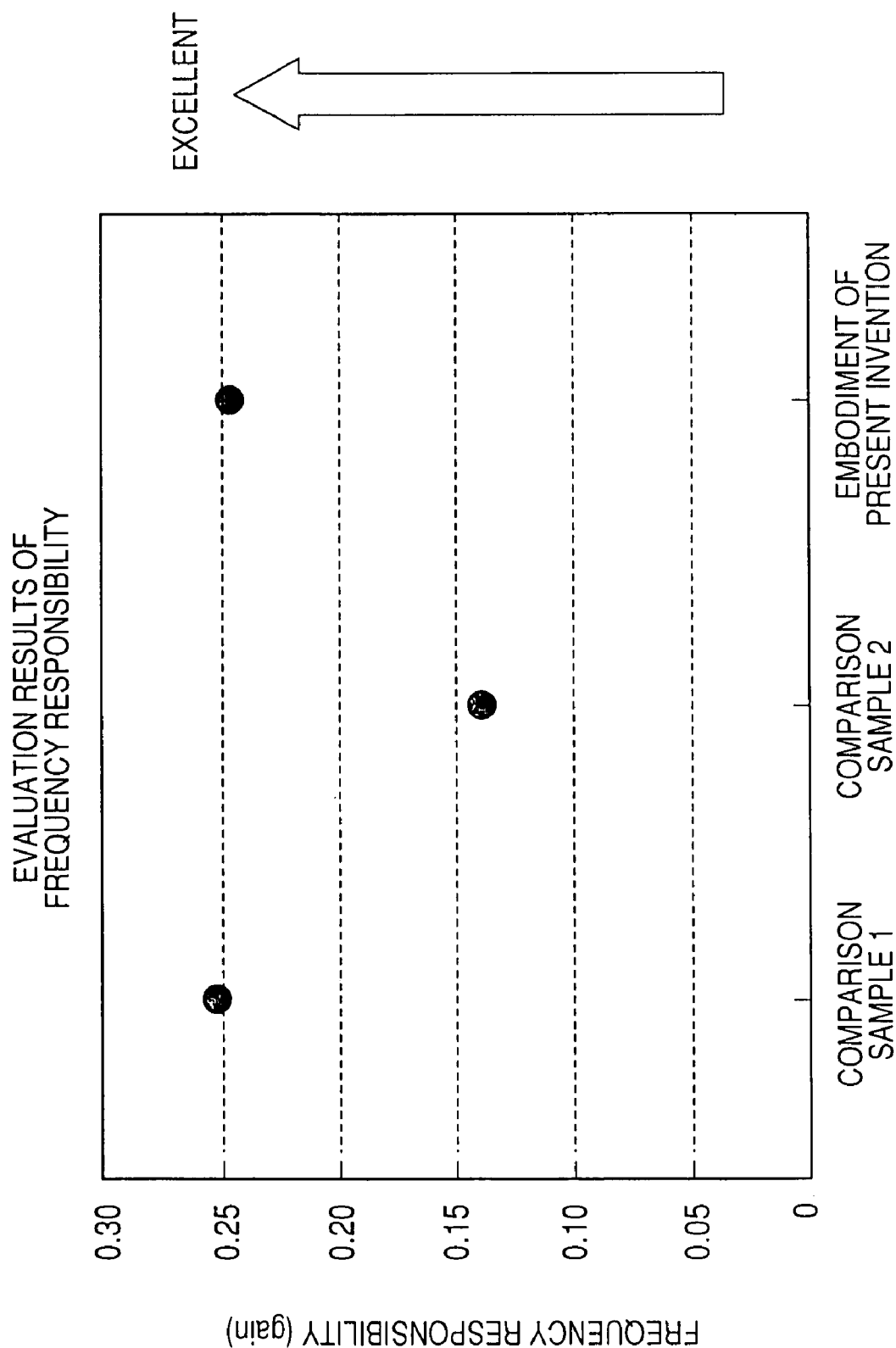
FIG. 7 shows evaluation results of the gas sensor according to the embodiment of the present invention and comparison examples in frequency responsible capability.

Hereinafter, various embodiments of the present invention will be described with reference to the accompanying drawings. In the following description of the various embodiments, like reference characters or numerals designate like or equivalent component parts throughout the several diagrams.

Embodiment

A description will be given of a gas sensor according to the embodiment of the present invention with reference to FIG. 1 and FIG. 2.

As shown in FIG. 1, the gas sensor 1 according to the embodiment is composed mainly of a gas sensor element 11 (or a concentration detection element), a housing 14, and a cover body (or a cylindrical cover body) of a double structure which is composed of an inner cover 12 and an outer cover 13. The gas sensor element 11 is supported by and fixed to the housing 14 in a gas flow passage (or gas pile, or a measuring gas passage) through which measuring gases such as exhaust gas flow. The inner cover 12 and the outer cover 13 are made of stainless or another material. Those covers 12 and 13 cover a part of the gas sensor element 11 which is exposed in the measuring gases such as exhaust gas.

The housing 14 is fixed to an exhaust gas pipe 8 joined to an internal combustion engine or another part of a vehicle by screws. The housing 14 supports a front end part of the gas sensor element 11 in the exhaust gas pipe 8, and supports a rear end part of the gas sensor element 11 in atmosphere (at the base side thereof).

Each of the inner cover 12 and the outer cover 13 forming the cover body of a cylindrical shape has a bottom part and a different radius. The inner cover 12 and the outer cover 13 are constructed in concentric configuration. The inner cover 12 has a hat or cup shape of an approximate constant radius. The upper part of the inner cover 12 is open and the bottom part thereof is closed by the bottom surface. An inner cover flange part 121 is formed at the upper end part of the inner cover 12. The inner cover flange part 121 projects toward the outer circumferential direction.

Like the inner cover 12, the outer cover 13 has a hat or cup shape of an approximate constant radius. The upper part of the outer cover 13 is open and the bottom part thereof is closed by the bottom surface. An outer cover flange part 131 is formed at the upper end part of the outer cover 13. The outer cover flange part 131 projects toward the outer circumferential direction.

Both the inner cover 12 and the outer cover 13 are mated and the inner cover flange part 121 and the outer cover flange part 131 are forcedly fixed together by caulk.

A radius slope part 122 having a taper shape is formed at the upper side surface of the inner cover 12. The bottom side of the radius taper part 122 is a large radius and the front side thereof is a small radius. Side surface opening parts 123 of the inner cover 12 are formed in the upward direction in the radius slope part 122. A plurality of bottom opening parts 125 is formed in the bottom surface 124 of the inner cover 12.

A plurality of side surface opening parts 132 are formed in the upper part of the side surface 130 of the outer cover 13 in order to introduce the measuring gases such as exhaust gas into a gap formed between the inner cover 12 and the outer cover 13. A radius tapered part 137 is formed at the lower part of the side surface 130 of the outer cover 13. The radius of the radius taper part 137 is gradually decreased toward the front part of the outer cover 13. The side surface of the outer cover 13 has a small radius part 136. The radius of the small radius part 136 has a tapered part 135 whose radius is gradually decreased toward the front end part of the outer cover 13 shown in FIG. 1.

A flat bottom part 134 of the outer cover 13 is formed at the front end part of the outer cover 13. A bottom surface opening part 133 is formed at the center part of the bottom surface 134 of the outer cover 13, which is positioned at the outside of the bottom opening part 125 of the inner cover 12.

A plurality of inner signal wirings 110 are connected to the gas sensor element 11 in order to perform data input/output operation and heater control operation. The inner signal wirings 110 are electrically connected to outer signal wirings 112 which are electrically connected to outside control devices through connection terminals 111.

The gas sensor element 11 is supported by and fixed to the housing 14 through an insulator 15, and covered with a sealing member 16.

The inner signal wirings 110 are covered with an insulation member 17. The outer signal wirings 112 are fixed to the gas sensor 1 through an insulation member 118. Those insulation members 117 and 118 are covered by a cover member 19 and tightly fixed to the housing 14.

The gas sensor 1 of the embodiment having the configuration described above is placed in and fixed to the wall surface 8 of the exhaust gas passage through an elastic member 20 by clamping housing screws 142 and housing nuts 143 so that the gas sensor element 11 covered with the inner cover 12 and the outer cover 13 of the cover body is placed in and exposed to the exhaust gas flow.

The gas sensor element 11 is a multilayer type oxygen sensor element and the like composed mainly of a solid electrolyte membrane of electric conductivity such as zirconia, a measuring electrode, a reference electrode, a reference gas introduction layer, and a heater layer which are laminated. The solid electrolyte membrane is placed or sandwiched between the measuring electrode, the reference electrode, the reference gas introduction layer, and the heater layer. According to the type of measuring gases, one of a Nox sensor, an air-fuel ratio sensor, and the like is selected.

A description will now be given of the configuration of each of the inner cover 12 and the outer cover 13 in the gas sensor 1 according to the embodiment of the present invention with reference to FIG. 2A to FIG. 2C.

FIG. 2A is a perspective view of the outer cover 13 of the gas sensor 1 according to the embodiment. FIG. 2B is a perspective view of the inner cover 12 of the gas sensor 1 according to the embodiment. FIG. 2C is a perspective view showing an assembly of the outer cover 13 shown in FIG. 2A and the inner cover 12 shown in FIG. 2B in the gas sensor 1 according to the embodiment.

Bottom surface opening parts 125 of a circle shape whose diameter is within a range of 0.5 mm to 2.0 mm are formed in the bottom surface 124 of the inner cover 12, and are also formed around the circumference of a circle whose diameter is within a range of 3.5 mm to 5.5 mm. In the configuration of the embodiment, each of the four bottom surface opening parts 125 is a circle shape of 1.0 mm diameter formed on the circumference of a circle of 4.5 mm diameter.

Plural tapered parts 122 are formed at the upper side surface of the inner cover 12, whose radius is gradually decreased from its base part to its front end part. The side surface opening part 123 is formed in each tapered part 122 in order to suck only the exhaust gas as the measuring gas while avoiding the invasion of water-drop contained in the measuring gas.

Each side surface opening part 123 of the inner cover 12 is positioned in front of the side surface opening part 132 of the outer cover 13 so that the side surface opening part 123 turns upward from the outside toward the inside of the inner cover 12. Each side surface opening part 123 is a concave part formed toward the inside direction in the base side of the inner cover 12. It is also acceptable to have slit parts in each concave part.

In the configuration of the embodiment, the six side surface opening parts 132 having an opening of 3.0 mm diameter are formed in regular order around the outer circumference of the outer cover 13.

It enables a taper angle of the tapered part 135 to have a value within a range of 70 to 120 angles, for example. It is preferred that the tapered part 135 has the taper angle of 94 angles.

It is possible to form the bottom surface opening part 133 of a circular shape of a diameter within a range of 0.5 mm to 3.0 mm, for example, at the center part of the bottom surface 134 of the outer cover 13. It is preferred that the side surface opening part 132 has the diameter of 1.0 mm.

As shown in FIG. 2C, the assembly of the inner cover 12 and the outer cover 13 together makes the a side surface gap 200 between the side surface 120 of the inner cover 12 and the side surface 130 of the outer cover 13, and further makes a bottom surface gap 201 between the bottom surface 125 of the inner cover 12 and the bottom surface 134 of the outer cover 13. It is preferred that the bottom surface gap 201 is set within a range of 0.5 mm to 5.5 mm (a value within a range of not less than 0.5 mm and not more than 5.5 mm).

FIG. 3 is a schematic view showing gas flow vectors indicating gas flow velocity (hereinafter, referred to as "the gas flow velocity vectors") in the gas sensor 1 according to the embodiment. FIG. 3 shows the gas flow velocity vectors obtained when the gas sensor 1 of the embodiment of the present invention is placed in the gas flow passage through which measuring gases at 25 m/sec which correspond to the flow speed of exhaust gas emitted from an internal combustion engine, which is rotating at 2000 r.p.m., mounted on a vehicle.

As clearly shown in FIG. 3, in the side surface opening part 132 of the outer cover 13, the measuring gas flow is made from the opening part 132 at the upstream side to the side surface gap 200 formed between the outer peripheral surface of the inner cover 12 and the inner peripheral surface of the outer cover 13. Further, in the side surface gap 200 at the upstream side of the measuring gases such as exhaust gas in the exhaust gas pipe 8, the measuring gases flow downward, namely, flow toward the bottom surface opening part 133 of the outer cover 13.

On the contrary, in the side surface gap 200 at the downstream side of the measuring gases such as exhaust gas in the exhaust gas pipe 8, the measuring gas flow upward toward the side surface opening part 132 of the outer cover 13. The measuring gases such as exhaust gas are discharged from the gas sensor 1 through the side surface opening part 132 of the outer cover 13.

At this time, the side surface opening part 123 of the inner cover 12 positioned at the upstream side of the measuring gas flow makes a negative pressure by the downward gas flow generated in the side surface gap 200. The side surface opening part 123 of the inner cover 12 at the upstream side of the exhaust gas flow acts as a pipe through which the gas introduced into the inner cover 12 is discharged into the side surface gap 200.

In addition, because the upward gas flow is made by the presence of, the side surface opening part 123 positioned at the downstream side of the exhaust gas flow as the measuring gas, the side surface opening part 123 acts as a gas sucking or introduction opening through which the exhaust gas as the measuring gas is introduced or sucked in the inside of the inner cover 12.

Still further, because the side surface opening parts 123 of the inner cover 12 open upward toward the inside of the inner cover 12, even if the measuring gases contain water drops, the water drops hardly enter into the side surface opening parts 123 of the inner cover 12, and the gas component only enters into the inner cover 12.

Furthermore, the gas flow from the bottom surface gap 201 into the inside of the inner cover 12 is made in the bottom surface opening parts 125 in the bottom surface 124 of the inner cover 12.

Still furthermore, the measuring gas flow collides with the tapered area formed in the tapered part 135 at the front end part of the outer cover 13, and this collision makes the measuring gas flow toward the downward of the front end part of the outer cover 13, and thereby makes a large pressure difference between the outside and the inside of the outer cover 13 at the bottom surface opening part 133 of the outer cover 13. The majority of the measuring gas flows from the inside to the outside of the outer cover 13 because such a pressure difference sucks the measuring gases downward. Thus, because the negative pressure generated by the bottom surface opening 133 of the outer cover 13 becomes large, the measuring gases in the bottom surface gap 201 are sucked through the bottom surface opening part 133 of the outer cover 13, and the invasion of water drops through the bottom surface opening part 133 can be prevented.

The measuring gases introduced into the side surface gap 200 through the side surface opening 132 of the outer cover 13 at the upstream side of the measuring gas flow are further introduced into the side surface gap 200 from the side surface opening part 123 of the inner cover 12 at the upstream side of the measuring gas flow, and the measuring gases are then discharged to the outside of the gas sensor 1 through the bottom surface opening part 133 of the outer cover 13 and the side surface opening 132 of the outer cover 13.

The measuring gases introduced from the side surface opening part 132 of the outer cover 13 into the side surface gap 200 is further introduced into the inside of the inner cover 12 through the bottom surface opening parts 125 of the inner cover 12 and the side surface opening parts 123 of the inner cover 12 at the downstream side of the measuring gas flow. The measuring gases are further introduced from the inside of the inner cover 12 to the side surface gap 200 through the side surface opening part 123 of the inner cover 12 at the upstream side of the measuring gas flow. The measuring gases are finally discharged to the outside of the gas sensor 1 through the bottom surface opening part 133 and the side surface opening 132 (at the downstream side of the measuring gas flow) of the outer cover 13.

Accordingly, because the measuring gases are contacted to the gas sensor element 11, and then introduced into the inner cover 12 and discharged to the outside of the inner cover 12, this configuration of the gas sensor 1 enables the gas sensor element 11 to have a quick responsiveness.

FIG. 4A shows a water proof testing apparatus as a simulator for performing water proof simulation of gas sensors. FIG. 4B shows an evaluation manner of evaluating the experimental results obtained by the simulator shown in FIG. 4. FIG. 5 shows an experimental manner of performing a frequency response test in order to verify the effects of the gas sensor.

As shown in FIG. 4A, the compressed air of 12.6 m/sec flow rate is supplied to a pipe 4, which corresponds to the actual exhaust gas pipe 3, while heating the measuring gas. The pipe 4 is placed in a level of 45 degree against a horizontal surface. Water drop of 0.2 cc is injected five times to the gas sensor 1. Such a water drop enters inside of the gas sensor 1 through the side surface opening 132 of the outer cover 13 or the bottom surface opening part 133 of the outer cover 13, and finally attached or adhered to the surface of the gas sensor element 11 in the gas sensor 1.

As shown in FIG. 4B, the trace or mark of the water drops adhered onto the surface of the gas sensor element 11 was photographed in order to obtain the image data. Those image data items are binarized and the area where the water drops adhered was calculated. The calculated area was used for verifying the water proof capability of the gas sensor.

In the experiment of verifying the water proof capability of the gas sensor 1 according to the embodiment of the present invention, the gas sensor 1 was placed in a level of 45 degree against a horizontal surface so that water drop is attached easily to the gas sensor 1 shown in FIG. 4A.

As shown in FIG. 5, the gas sensor 1 was placed in an exhaust gas flow passage to be mounted on a direct injection type engine of a three litter displacement and six covers. In the experiment, the output of the gas sensor 1 was measured under the condition of engine speed of 2000 r.p.m. while periodically varying the air-fuel ratio within a rage from 1.1 to 0.9 under the control frequency of 4.16 Hz, where a reference air-fuel ratio of 1. The FET analysis was performed for the obtained output of the gas sensor 1 in order to obtain the gain of the gas sensor.

An experimental sample is the gas sensor 1 according to the embodiment of the present invention shown in FIG. 1.

Figure 10:
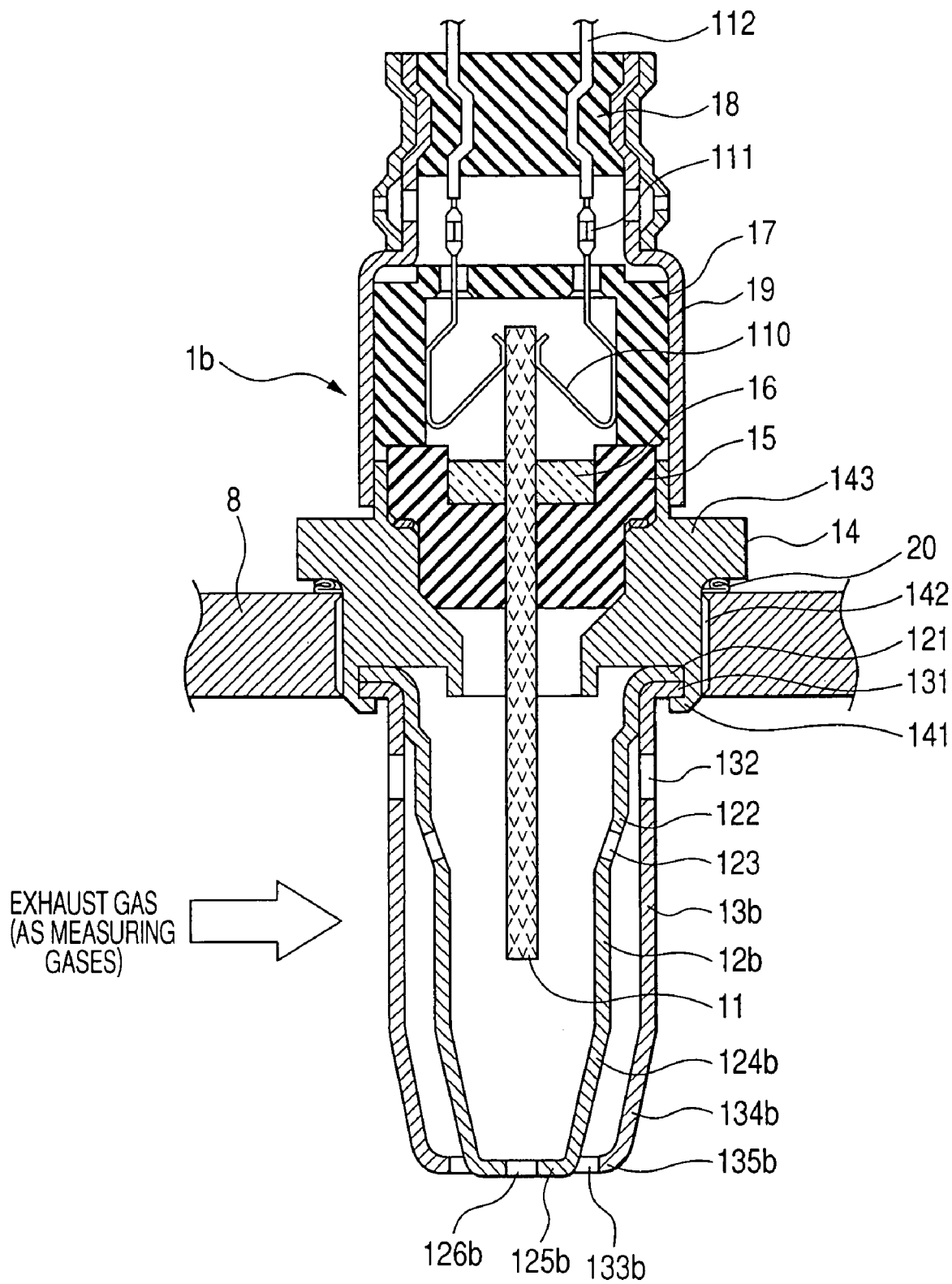
FIG. 10 is a sectional view showing a configuration of a related-art gas sensor as a first comparison example.
Figure 11:
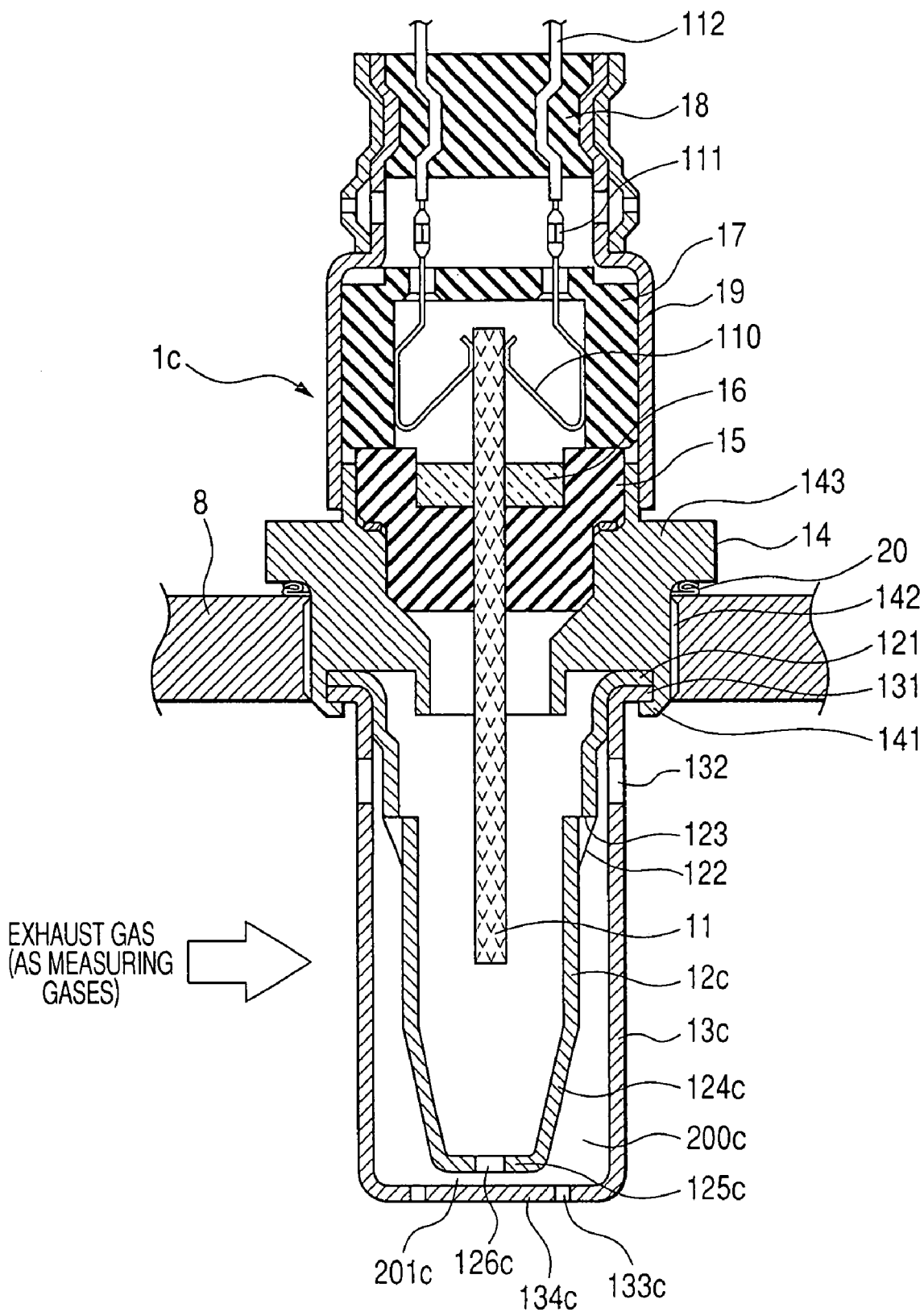
FIG. 11 is a sectional view showing a configuration of another related-art gas sensor as a second comparison example.

A first comparison sample is the gas sensor 1b having the configuration shown in FIG. 10, and a second comparison sample is the gas sensor 1c having the configuration shown in FIG. 11.

In those gas sensors 1, 1b, and 1c to be tested, the same reference numbers or characters are used for the same components and the explanation of those same components are omitted here.

The cover body of the gas sensor 1b (as the first comparison sample) shown in FIG. 10 has a double cover construction composed mainly of the inner cover 12b and the outer cover 13b of a different radius and being constructed in concentric configuration. At the center part of the inner cover 12b and the bottom surface 125b, the bottom surface opening part 126b of the inner cover 12b is formed. Further, the plurality of opening parts 132 are formed at the upper part of the inner cover 12b in order to introduce the measuring gases into the inside of the gas sensor 12b. The bottom surface opening part 133b is formed in the middle part of the bottom surface 135b of the outer cover 13b, where the bottom surface opening part 133b and the bottom surface opening part 126b of the inner cover 12b are constructed in concentric configuration.

On the contrary, The cover body of the gas sensor 1C (as the second comparison sample) shown in FIG. 11 has a double cover construction composed mainly of the inner cover 12c and the outer cover 13c of a different radius and being configured in concentric configuration. In the cover body, the side surface gap 200c is formed between the outer peripheral surface of the inner cover 12c and the inner peripheral surface of the outer cover 13c. In the cover body, the side surface opening part 123 is formed at the upper side of the inner cover 12c so that the direction of the opening part 123 enters upwards from the outside of the inner cover 12c to the inside of the inner cover 12c. Further, the bottom surface opening part 126c of the inner cover 12c is formed at the center of the bottom surface 125c of the inner cover 12c. The plurality of side surface opening parts 132 are formed at the upper part of the side surface in order to introduce the gas into the side surface gap 200c. The bottom surface 134c of the outer cover 13c is placed below the bottom surface 125c of the inner cover 12c, and the bottom surface gap is formed between the bottom surface 125c of the inner cover 12c and the bottom surface 134c of the outer cover 13c, and the plurality of bottom surface opening parts 133c are formed at the outer circumference part of the bottom surface 134c, which are positioned outside when compared with the position of the bottom surface opening part 126c.

As shown in FIG. 6, the gas sensor 1 of the embodiment according to the present invention has a small water-drop adhesion area and a superior water proof capability when compared with the first comparison sample. Further, as can be clearly understood form the evaluation results shown FIG. 6, when compared with the second comparison sample, the gas sensor 1 of the embodiment according to the present invention has a small water-drop adhesion area and a superior water proof capability.

As can be clearly understood from the evaluation results shown FIG. 7, there is almost no difference in frequency responsiveness between the gas sensor 1 of the embodiment according to the present invention and the first comparison sample, and the gas sensor 1 according to the present invention has a superior frequency responsiveness when compared with that of the second comparison sample.

According to the present invention, it is possible to improve and enhance the water proof capability of the gas sensor having a good frequency responsiveness, and at the same time, it is possible to improve the frequency responsiveness of the gas sensor having a good water proof capability.

Figure 8:
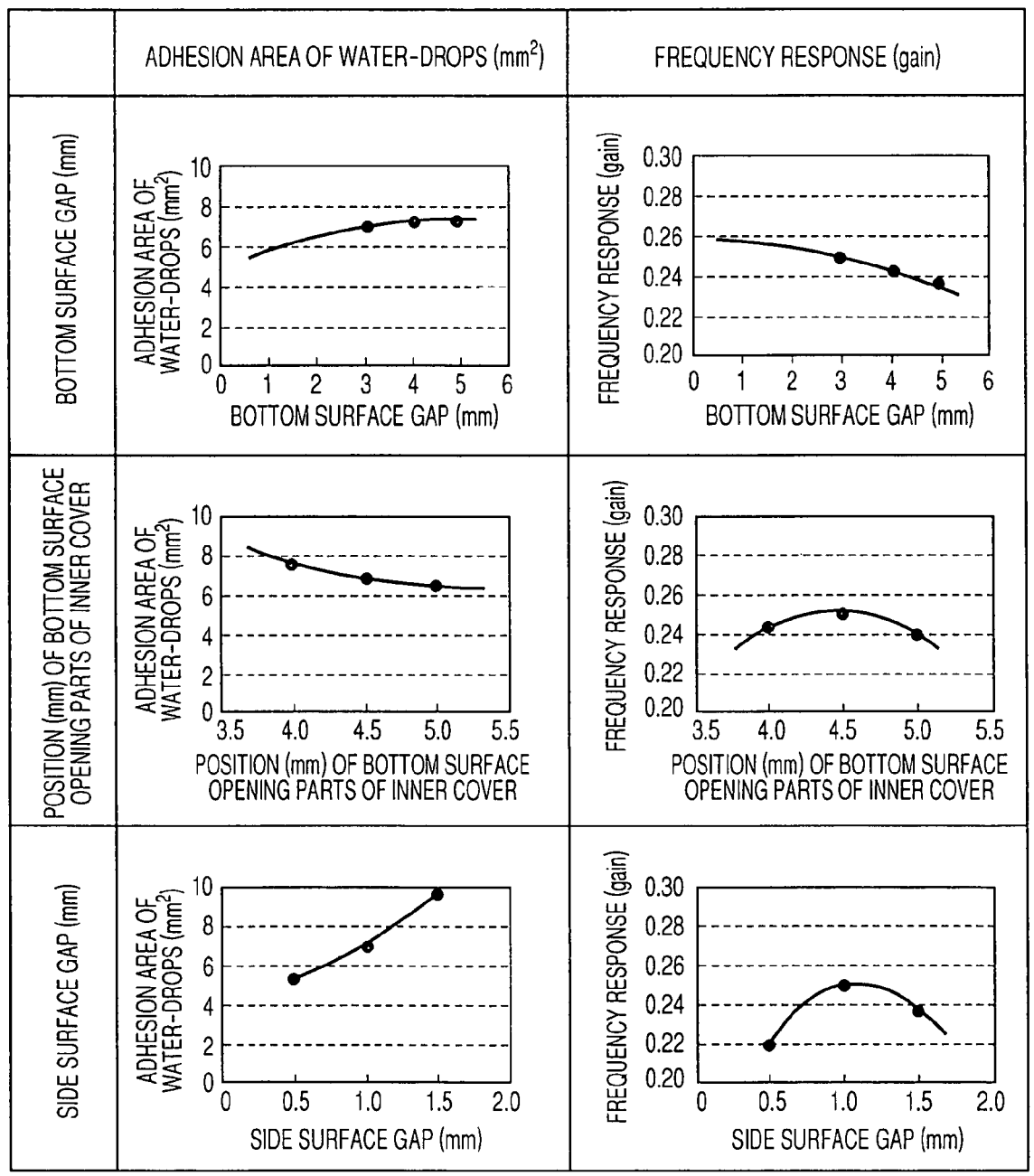
FIG. 8 shows the best configuration of the gas sensor under various parameters according to the present invention.

A description will now be given of optimum parameters of the gas sensor according to the present invention with reference to FIG. 8.

The water-drop adhesion area onto the gas sensor element is not almost changed according to the size of the bottom surface gap formed between the bottom surfaces of the outer cover and the inner cover. The bottom surface gap of 3.0 mm has the maximum frequency responsiveness. Although it is possible to have the bottom surface gap within a range of 0.5 to 5.5 mm, it is more preferred to have the bottom surface gap of 3.0 mm.

Under the conditions in which the bottom surface opening part of the inner cover has a diameter in concentric configuration with the inner cover, and the interval of the bottom surface opening parts of the inner cover is changed in 4.0 mm, 4.5 mm, and 5.0mm, the water-drop adhesion area is decreased according to decreasing the interval of the bottom surface opening parts of the inner cover. The gas sensor in which the interval of the bottom surface opening parts of the inner cover is 4.5 mm can provide the most superior frequency responsiveness.

It is preferred to set the interval of the bottom surface opening parts of the inner cover within a range of 3.5 mm to 5.5 mm, and more preferably, to set the bottom surface opening parts of the inner cover to 4.5 mm.

When the side surface gap formed between the side surface of the inner cover and the side surface of the outer cover is varied from 0.5 mm to 1.5 mm, the more the side surface gap increases, the more the size of the water-drop adhesion area. It is preferred to set the side surface gap to 1.0 mm in order to have the optimum frequency responsiveness.

A description will now be given of the optimum configurations of the cover body composed of the inner cover and the outer cover of the gas sensor according to the present invention with reference to FIG. 9A to FIG. 9D. FIG. 9A to FIG. 9D show the optimum configurations of the gas sensor according to the present invention.

Figure 9A:
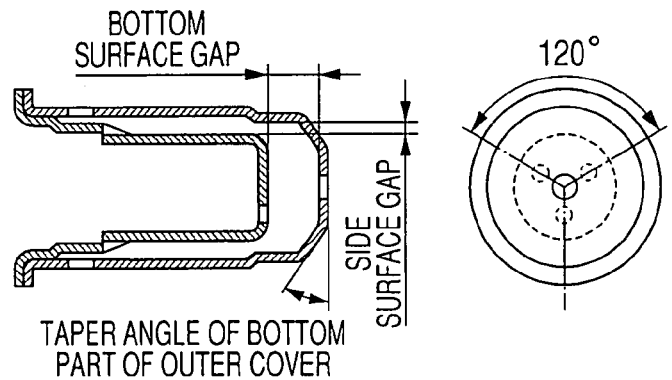
FIGS. 9A, 9B, 9C and 9D show optimum configurations of the gas sensor according to the present invention.

In the configuration shown in FIG. 9A, the three bottom surface opening parts of the inner cover are placed at a same interval in concentric with the inner cover.

Figure 9B:
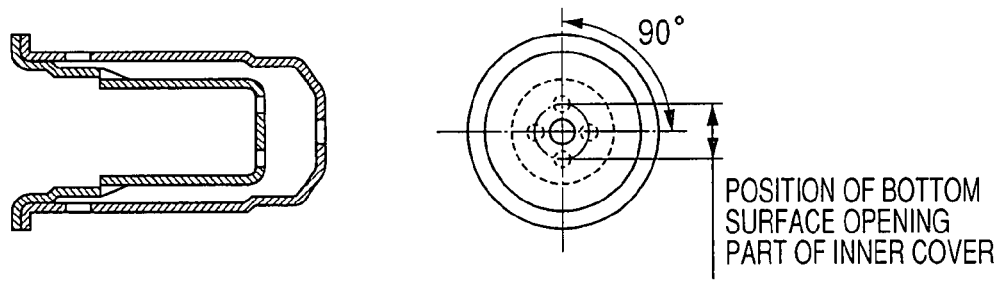

The configuration shown in FIG. 9B corresponds to the gas sensor of the embodiment of the present invention, the four bottom surface opening parts of the inner cover are placed at a same interval in concentric with the inner cover.

Figure 9C:
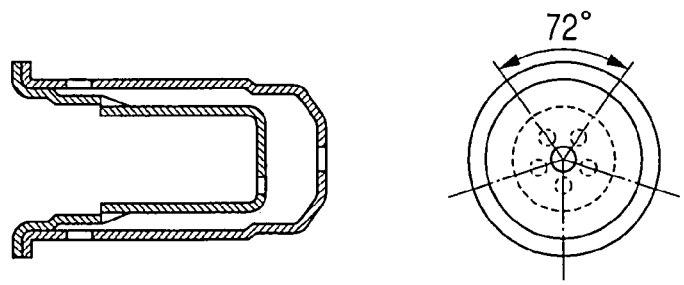

In the configuration shown in FIG. 9C the five bottom surface opening parts of the inner cover are placed at a same interval in concentric with the inner cover.

Figure 9D:
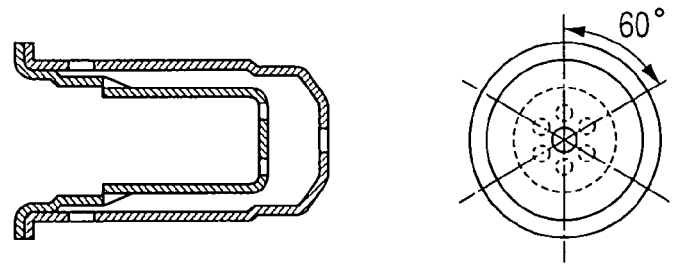

In the configuration shown in FIG. 9D, the six bottom surface opening parts of the inner cover are placed at a same interval in concentric with the inner cover.

According to the present invention, the cover body is composed of the inner cover and the outer cover which being constructed in concentric configuration. However, the concept of the present invention is not limited by such a configuration. For example, it is acceptable to have a cover body of a triple cover configuration, in which the outer cover accommodating the inner cover is covered with an additional cover capable of transmitting the measuring gases to the outer cover. This configuration has a superior thermal insulation capability. Because this configuration can provide a stable activation state of the gas sensor element, it is possible to further increase the frequency responsiveness.

Although the embodiment of the present invention explains the multilayer type gas sensor such as a multilayer type oxygen sensor, it is possible to apply the concept of the present invention to other types of gas sensors such as a cup-shaped type gas sensor, for example.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalent thereof.

What is claimed is:

1. A gas sensor comprising:
a concentration detection element capable of detecting a concentration of a specified gas contained in measuring gases which pass through a measuring gas passage;
a housing accommodating the concentration detection element and fixing the concentration detection element to the measuring gas passage so that the concentration detection element is exposed in a measuring gas flow; and
a cylindrical cover body having a bottom part, accommodating a part of the concentration detection element exposed in the measuring gas flow, and the cylindrical cover body having a plural cylinder configuration composed of at least an inner cover and an outer cover of a different radius constructed in a concentric configuration to each other,
wherein in the cylindrical cover body,
a side surface gap is formed between an outer peripheral surface of the inner cover and an inner peripheral surface of the outer cover,
side surface opening parts of the inner cover are formed at the upper part of the side surface of the inner cover so that the opening direction of each side surface opening part of the inner cover turns upward from the outside of the inner cover toward the inside of the inner cover,
a plurality of bottom surface opening parts of the inner cover constructed in concentric with an axis of the inner cover is formed in the bottom surface of the inner cover,
a plurality of side surface opening parts through which the measuring gases are introduced into the side surface gap is formed at the upper part of the side surface of the outer cover,
a bottom surface gap is formed between the bottom surface of the outer cover and the bottom surface of the inner cover in which the bottom surface of the outer cover is positioned below the bottom surface of the inner cover,
a bottom surface opening part is formed at a center of the bottom surface of the outer cover, close in position to the center of the bottom surface rather than the bottom surface opening parts of the inner cover.

2. The gas sensor according to claim 1, wherein the outer cover has a tapered part at a front end part of the outer cover, and a radius of the tapered part of the outer cover is gradually decreased toward the front end part of the outer cover.

3. The gas sensor according to claim 2, wherein one of a tapered part and a plurality of concave parts is formed at the upper part of the inner cover where a radius of the tapered part is reduced toward the front end of the inner cover and each concave part is concave toward the inside of the inner cover, and each of the side surface opening parts of the inner cover has a slit shaped opening and is formed in one of the tapered part and the concave part.

4. The gas sensor according to claim 2, wherein a radius decreased part is formed at the side surface in a front end part of the outer cover so that the base part of the radius decreased part is larger in radius than the front end part of the radius decreased part, and the side surface gap is small near the bottom surface of the inner cover.

5. The gas sensor according to claim 2, wherein the bottom surface opening part of the outer cover is a circular shape whose diameter is set within a range of 0.5 mm to 3.0 mm.

6. The gas sensor according to claim 2, wherein the bottom surface gap formed between the bottom surface of the inner cover and the bottom surface of the outer cover is set within a range of 0.5 mm to 5.5 mm.

7. The gas sensor according to claim 2, wherein the plurality of bottom surface opening parts of the inner cover is formed in the bottom surface of the inner cover having a circular shape whose diameter is set within a range of 3.5 mm to 5.5 mm, and the axis of the bottom surface of a circular shape of the inner cover is concentric with the axis of the outer cover.

8. The gas sensor according to claim 2, wherein a radius of the opening of each bottom surface opening part of the inner cover has a circular shape whose diameter is set within a range of 0.5 m to 2.0 mm.

9. The gas sensor according to claim 2, wherein the plurality of bottom surface opening parts are three openings placed at a regular interval in concentric with the axis of the inner cover.

10. The gas sensor according to claim 2, wherein the side surface gap is set within a range of 0.5 mm to 1.5 mm.

11. The gas sensor according to claim 1, wherein one of a tapered part and a plurality of concave parts is formed at the upper part of the inner cover where a radius of the tapered part is reduced toward the front end of the inner cover and each concave part is concave toward the inside of the inner cover, and each of the side surface opening parts of the inner cover has a slit shaped opening and is formed in one of the tapered part and the concave part.

12. The gas sensor according to claim 1, wherein a radius decreased part is formed at the side surface in a front end part of the outer cover so that the base part of the radius decreased part is larger in radius than the front end part of the radius decreased part, and the side surface gap is small near the bottom surface of the inner cover.

13. The gas sensor according to claim 1, wherein the bottom surface opening part of the outer cover is a circular shape whose diameter is set within a range of 0.5 mm to 3.0 mm.

14. The gas sensor according to claim 1, wherein the bottom surface gap formed between the bottom surface of the inner cover and the bottom surface of the outer cover is set within a range of 0.5 mm to 5.5 mm.

15. The gas sensor according to claim 1, wherein the plurality of bottom surface opening parts of the inner cover is formed in the bottom surface of the inner cover having a circular shape whose diameter is set within a range of 3.5 mm to 5.5 mm, and the axis of the bottom surface of a circular shape of the inner cover is concentric with the axis of the outer cover.

16. The gas sensor according to claim 1, wherein a radius of the opening of each bottom surface opening part of the inner cover has a circular shape whose diameter is set within a range of 0.5 m to 2.0 mm.

17. The gas sensor according to claim 1, wherein the plurality of bottom surface opening parts are three openings placed at a regular interval in concentric with the axis of the inner cover.

18. The gas sensor according to claim 1, wherein the side surface gap is set within a range of 0.5 mm to 1.5 mm.

* * * * *